US009603923B2

(12) United States Patent
Johannes et al.

(10) Patent No.: US 9,603,923 B2
(45) Date of Patent: Mar. 28, 2017

(54) UNIVERSAL CARRIER FOR TARGETING MOLECULES TO GB3 RECEPTOR EXPRESSING CELLS

(71) Applicants: INSTITUT CURIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE PIERRE ET MARIE CURIE (PARIS VI), Paris (FR)

(72) Inventors: Ludger Johannes, Courbevoie (FR); Eric Tartour, Paris (FR); Bruno Goud, Paris (FR); Wolf Herve Fridman, Paris (FR)

(73) Assignees: INSTITUT CURIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE PIERRE ET MARIE CURIE (PARIS VI), Paris (FR)

( * ) Notice: Subject to any disclaimer, the term of this patent is extended or adjusted under 35 U.S.C. 154(b) by 0 days.

(21) Appl. No.: 14/478,687

(22) Filed: Sep. 5, 2014

(65) Prior Publication Data

US 2015/0045536 A1    Feb. 12, 2015

Related U.S. Application Data

(60) Division of application No. 12/569,007, filed on Sep. 29, 2009, now Pat. No. 8,852,612, which is a division of application No. 10/628,415, filed on Jul. 29, 2003, now Pat. No. 7,632,514, which is a continuation of application No. PCT/EP02/01627, filed on Feb. 1, 2002.

(30) Foreign Application Priority Data

Feb. 1, 2001 (EP) .................................... 01400255

(51) Int. Cl.
| | | |
|---|---|---|
| A61K 39/38 | (2006.01) | |
| A61K 39/385 | (2006.01) | |
| C07K 14/25 | (2006.01) | |
| A61K 38/00 | (2006.01) | |
| A61K 48/00 | (2006.01) | |
| A61K 39/00 | (2006.01) | |

(52) U.S. Cl.
CPC ............ *A61K 39/385* (2013.01); *C07K 14/25* (2013.01); *A61K 38/00* (2013.01); *A61K 48/00* (2013.01); *A61K 2039/6037* (2013.01); *A61K 2039/627* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,810,643 A | 3/1989 | Souza | |
| 5,994,311 A | 11/1999 | Eichner et al. | |
| 6,613,882 B1 | 9/2003 | Goud et al. | |
| 6,652,857 B2 | 11/2003 | Williams et al. | |
| 6,777,202 B2 | 8/2004 | Lubitz et al. | |
| 6,855,321 B1 | 2/2005 | Rappuoli et al. | |
| 7,488,809 B2 | 2/2009 | Goud et al. | |
| 7,632,514 B2 | 12/2009 | Johannes et al. | |
| 7,718,601 B2 | 5/2010 | Johannes et al. | |
| 7,981,400 B2 | 7/2011 | Johannes et al. | |
| 8,293,245 B2 | 10/2012 | Smith et al. | |
| 8,313,731 B2 | 11/2012 | Johannes et al. | |
| 8,524,652 B2 | 9/2013 | Goud et al. | |
| 8,685,408 B2 | 4/2014 | Tartour | |
| 8,846,058 B2 * | 9/2014 | Smith ................ | A61K 39/0258 424/185.1 |
| 8,852,612 B2 * | 10/2014 | Johannes ............. | A61K 39/385 424/236.1 |
| 8,969,529 B2 * | 3/2015 | O'Brien ............. | C07K 16/1232 435/69.1 |

(Continued)

FOREIGN PATENT DOCUMENTS

| | | |
|---|---|---|
| EP | 1229045 A1 | 8/2002 |
| EP | 1386927 A1 | 2/2004 |

(Continued)

OTHER PUBLICATIONS

Garcia-Castillo et al, Journal of Cell Science (2015) 128, 2373-2387 doi:10.1242/jcs.169383.*
Andrade et al, Human Vaccines & Immunotherapeutics 10:10, 2864-2874; Oct. 2014.*
Bartkowski et al., "Aggregation of Recombinant Bovine Granulocyte Colony Stimulating Factor in Solution", Journal of Protein Chemistry, vol. 21, No. 3, Mar. 2002, pp. 137-143.
Bast et al., "The identification of three biologically relevant globotriaosyl ceramide receptor binding sites on the Verotoxin 1 B subunit", Molecular Microbiology, vol. 32, No. 5, 1999, pp. 953-960.

(Continued)

*Primary Examiner* — Nita M Minnifield
(74) *Attorney, Agent, or Firm* — Birch, Stewart, Kolasch & Birch, LLP

(57) ABSTRACT

The present invention concerns an universal polypeptidic carrier for targeting directly or indirectly a molecule to Gb3 receptor expressing cells and having the following formula STxB-Z(n)-Cys, wherein:
STxB is the Shiga Toxin B subunit or a functional equivalent thereof,
Z is an amino-acid devoided of sulfydryl group, n being 0, 1 or a polypeptide,
Cys is the amino-acid Cysteine,
and the use thereof for MHC class I and MHC class II presentation of antigens.

11 Claims, 10 Drawing Sheets

(56) References Cited

U.S. PATENT DOCUMENTS

| | | | |
|---|---|---|---|
| 9,034,868 B2* | 5/2015 | Gillet | A61K 31/167 514/220 |
| 9,226,957 B2* | 1/2016 | Bottje | A61K 39/0275 |
| 2004/0047883 A1 | 3/2004 | Goud et al. | |
| 2004/0110935 A1 | 6/2004 | Johannes et al. | |
| 2006/0008475 A1 | 1/2006 | Johannes et al. | |
| 2009/0035330 A1 | 2/2009 | Dewerchin | |
| 2009/0092578 A1 | 4/2009 | Su et al. | |
| 2010/0196417 A1 | 8/2010 | Tartour | |
| 2010/0196418 A1* | 8/2010 | Johannes | A61K 39/385 424/197.11 |
| 2010/0266672 A1 | 10/2010 | Garcon et al. | |
| 2010/0322913 A1 | 12/2010 | Goud et al. | |
| 2010/0329992 A1 | 12/2010 | Johannes et al. | |
| 2011/0318357 A1* | 12/2011 | O'Brien | C07K 16/1232 424/139.1 |
| 2015/0045536 A1* | 2/2015 | Johannes | A61K 39/385 530/324 |

FOREIGN PATENT DOCUMENTS

| | | |
|---|---|---|
| EP | 1938836 A1 | 7/2008 |
| FR | 2766193 A1 | 1/1999 |
| WO | WO 95/11998 A1 | 5/1995 |
| WO | WO 99/03881 A2 | 1/1999 |
| WO | WO 02/060937 A1 | 8/2002 |
| WO | WO 2004/016148 A2 | 2/2004 |
| WO | WO 2008/080926 A1 | 7/2008 |

OTHER PUBLICATIONS

Calderwood et al., "Nucleotide sequence of the Shiga-like toxin genes of Escherichia coli", Proc. Natl. Acad. Sci. USA, Biochemistry, vol. 84, Jul. 1987, pp. 4364-4368.
Carlsson et al., "Protein Thiolation and Reversible Protein-Protein Conjugation", Biochem. J., vol. 173, 1978, pp. 723-737.
Dubos et al., "Preparation and Properties of Shiga Toxin and Toxoid", J. Exp. Med., vol. 56, 1946, pp. 143-156.
Gaidamakova et al., "Molecular vehicle for target-mediated delivery of therapeutics and diagnostics", Journal of Controlled Release, vol. 74, Issues 1-3, Jul. 6, 2001, pp. 341-347.
Gariépy, "The use of Shiga-like toxin 1 in cancer therapy", Critical Reviews in Oncology/Hematology, vol. 39, 2001, pp. 99-106.
Hagnerelle et al., "Two-dimensional structures of the Shiga toxin B-subunit and of a chimera bound to the glycolipid receptor Gb3", Journal of Structural Biology, vol. 139, 2002, pp. 113-121.
Haicheur et al., "The B Subunit of Shiga Toxin Fused to a Tumor Antigen Elicits CTL and Targets Dendritic Cells to Allow MHC Class I-Restricted Presentation of Peptides Derived from Exogenous Antigens", The Journal of Immunology, vol. 165, 2000, pp. 3301-3308.
Herold et al., "Shiga toxin-encoding bacteriophages-genomes in motion", International Journal of Medical Microbiology, vol. 294, 2004, pp. 115-121.
International Search Report, dated Jul. 23, 2002, for International Application No. PCT/EP02/01627.
Ishikawa et al., "The Substitution of Cysteine 17 of Recombinant Human G-CSF with Alanine Greatly Enhanced its Stability", Cell Structure and Function, vol. 17, 1992, pp. 61-65.
Johannes et al., "Retrograde Transport of KDEL-bearing B-fragment of Shiga Toxin", The Journal of Biological Chemistry, vol. 272, No. 31, Aug. 1, 1997, pp. 19554-19561.
Jones et al., "Variable linking region immunogenicity using malarial peptide carrier protein conjugates of defined composition", Immunology Letters, vol. 26, 1990, pp. 285-290.
Kim et al., "Tetanus toxin C-fragment as a universal carrier protein for conjugate vaccines", Abstracts of the Interscience Conference on Antimicrobial Agents and Chemotherapy, vol. 43, 2003, p. 294, abstract only provided.
Lee et al., "Major histocompatibility complex class I presentation of exogenous soluble tumor antigen fused to the B-fragment of Shiga toxin", Eur. J. Immunol., vol. 28, 1998, pp. 2726-2737.

Ling et al., "A mutant Shiga-like toxin IIe bound to its receptor Gb3: structure of a group II Shiga-like toxin with altered binding specificity", Structure, vol. 8, No. 3, Feb. 22, 2000, pp. 253-264.
Ling et al., "Structure of the Shiga-like Toxin I B-Pentamer Complexed with an Analogue of Its Receptor Gb3", Biochemistry, vol. 37, 1998 (Published on the Web Feb. 3, 1998), pp. 1777-1788.
Lu et al., "Isomers of Epidermal Growth Factor with Ser → Cys Mutation at the N-Terminal Sequence: Isomerization, Stability, Unfolding, Refolding, and Structure", Biochemistry, vol. 44, 2005 (Published on the Web Oct. 22, 2005), pp. 15032-15041.
Makino et al., "Genetically modified Shiga toxin 2e (Stx2e) producing Escherichia coli is a vaccine candidate for porcine edema disease", Microbial Pathogenesis, vol. 31, 2001, pp. 1-8.
Mallard et al., "Direct Pathway from Early/Recycling Endosomes to the Golgi Apparatus Revealed through the Study of Shiga Toxin B-fragment Transport", The Journal of Cell Biology, vol. 143, No. 4, Nov. 16, 1998, pp. 973-990.
Noakes et al., "Exploiting retrograde transport of Shiga-like toxin 1 for the delivery of exogenous antigens into the MHC class I presentation pathway", FEBS Letters, vol. 453, 1999, pp. 95-99.
Ohmura-Hoshino et al., "Non-toxic Stx derivatives from Escherichia coli possess adjuvant activity for mucosal immunity", Vaccine, vol. 22, 2004 (Available online Apr. 22, 2004), pp. 3751-3761.
O'Loughlin et al., "Effect of Shiga toxin and Shiga-like toxins on eukaryotic cells", Microbes and Infection, vol. 3, 2001, pp. 493-507.
Partial European Search Report, dated Feb. 4, 2002, for European Application No. 01400255.4.
Perera et al., "Identification of Three Amino Acid Residues in the B Subunit of Shiga Toxin and Shiga-Like Toxin Type II That Are Essential for Holotoxin Activity", Journal of Bacteriology, vol. 173, No. 3, Feb. 1991, pp. 1151-1160.
Pruimboom-Brees et al., "Cattle lack vascular receptors for Escherichia coli 0157:H7 Shiga toxins", PNAS, vol. 97, No. 19, Sep. 12, 2000, pp. 10325-10329.
Rapak et al., "Retrograde transport of mutant ricin to the endoplasmic reticulum with subsequent translocation to cytosol", Proc. Natl. Acad. Sci. USA, Cell Biology, vol. 94, Apr. 1997, pp. 3783-3788.
Ryd et al., "Induction of a humoral immune response to a Shiga toxin B subunit epitope expressed as a chimeric LamB protein in a Shigella flexneri live vaccine strain", Microbial Pathogenesis, vol. 12, 1992, pp. 399-407.
Sandvig et al., "Retrograde Transport from the Golgi Complex to the ER of Both Shiga Toxin and the Nontoxic Shiga B-fragment Is Regulated by Butyric Acid and cAMP", The Journal of Cell Biology, vol. 126, No. 1, Jul. 1994, pp. 53-64.
Sandvig et al., "Retrograde transport of endocytosed Shiga toxin to the endoplasmic reticulum", Nature, vol. 358, Aug. 6, 1992, pp. 510-512.
Sandvig et al., "Transport of protein toxins into cells: pathways used by ricin, cholera toxin and Shiga toxin", FEBS Letters, vol. 529, 2002 (First published online Aug. 14, 2002), pp. 49-53.
Sandvig, "Shiga toxins", Toxicon, vol. 39, 2001, pp. 1629-1635.
Schelte et al., "Differential Reactivity of Maleimide and Bromoacetyl Functions with Thiols: Application to the Preparation of Liposomal Diepitope Constructs", Bioconjugate Chem, vol. 11, 2000, pp. 118-123.
Schoen et al., "Bacteria as DNA vaccine carriers for genetic immunization", International Journal of Medical Microbiology, vol. 294, 2004, pp. 319-335.
Seidah et al., "Complete Amino Acid Sequence of Shigella Toxin B-chain", The Journal of Biological Chemistry, vol. 261, No. 30, Oct. 25, 1986, pp. 13928-13931.
Shigematsu et al., "Site-directed lipid modification of IgG-binding protein by intracellular bacterial lipoprotein process", Journal of Biotechnology, vol. 75, 1999, pp. 23-31.
Stenmark et al., "Peptides Fused to the Amino-Terminal End of Diphtheria Toxin Are Translocated to the Cytosol", The Journal of Cell Biology, vol. 113, No. 5, Jun. 1991, pp. 1025-1032.
Su et al., "Construction of Stable LamB-Shiga Toxin B Subunit Hybrids: Analysis of Expression in Salmonella typhimurium aroA

(56) References Cited

OTHER PUBLICATIONS

Strains and Stimulation of B Subunit-Specific Mucosal and Serum Antibody Responses", Infection and Immunity, vol. 60, No. 8, Aug. 1992, pp. 3345-3359.
Su et al., "Extracellular export of Shiga toxin B-subunit/haemolysin A (C-terminus) fusion protein expressed in *Salmonella typhimurium* aroA-mutant and stimulation of B-subunit specific antibody . . . ," Microbial Pathogenesis, vol. 13, No. 6, Dec. 1992, pp. 465-476, abstract only provided.
Tarragó-Trani et al., "A method for the purification of Shiga-like toxin 1 subunit B using a commercially available galabiose-agarose resin", Protein Expression and Purification, vol. 38, 2004 (Available online Oct. 5, 2004), pp. 170-176.
Tarragó-Trani et al., "Shiga-like Toxin Subunit B (SLTB)-Enhanced Delivery of Chlorin e6 (Ce6) Improves Cell Killing", Photochemistry and Photobiology, vol. 82, 2006 (Published online Nov. 7, 2005), pp. 527-537.
Tzschaschel et al., "Towards a vaccine candidate against Shigella dysenteriae 1: expression of the Shiga toxin B-subunit in an attenuated Shigella flexneri aroD carrier strain", Microbial Pathogenesis, vol. 21, 1996, pp. 277-288.
U.S. Advisory Action, dated Jan. 19, 2012, for U.S. Appl. No. 12/569,007.
U.S. Advisory Action, dated Oct. 13, 2006, for U.S. Appl. No. 10/628,415.
U.S. Notice of Allowance, dated Jun. 29, 2009, for U.S. Appl. No. 10/628,415.
U.S. Notice of Allowance, dated Jun. 6, 2014, for U.S. Appl. No. 12/569,007.
U.S. Office Action, dated Apr. 12, 2006, for U.S. Appl. No. 10/628,415.
U.S. Office Action, dated Apr. 25, 2007, for U.S. Appl. No. 10/628,415.
U.S. Office Action, dated Aug. 2, 2005, for U.S. Appl. No. 10/628,415.
U.S. Office Action, dated Feb. 4, 2011, for U.S. Appl. No. 12/569,007.
U.S. Office Action, dated Jan. 27, 2005, for U.S. Appl. No. 10/628,415.
U.S. Office Action, dated Nov. 1, 2013, for U.S. Appl. No. 12/569,007.
U.S. Office Action, dated Oct. 31, 2008, for U.S. Appl. No. 10/628,415.
U.S. Office Action, dated Oct. 7, 2011, for U.S. Appl. No. 12/569,007.
Vingert et al., "The Shiga toxin B-subunit targets antigen in vivo to dendritic cells and elicits anti-tumor immunity", Eur. J. Immunol, vol. 36, 2006, pp. 1124-1135.
Waldrep, "New Aerosol Drug Delivery Systems for the Treatment of Immune-Mediated Pulmonary Diseases", Drugs of Today, vol. 34, No. 6, 1998, pp. 549-561.
Xu et al., "Immunogenicity of an HIV-1 gag DNA vaccine carried by attenuated Shigella", Vaccine, vol. 21, 2003, pp. 644-648.

* cited by examiner

UNIVERSAL CARRIER FOR TARGETING MOLECULES TO GB3 RECEPTOR EXPRESSING CELLS

This is a divisional of co-pending U.S. patent application Ser. No. 12/569,007 filed Sep. 29, 2009, which is a divisional of U.S. patent application Ser. No. 10/628,415 filed Jul. 29, 2003, issued as U.S. Pat. No. 7,632,514 on Dec. 15, 2009, which is a continuation application of PCT Application No. PCT/EP02/01627 filed on Feb. 1, 2002, and which claims priority under 35 U.S.C. §119(a) to Patent Application No. EP01400255.4 filed in Europe on Feb. 1, 2001, the entire contents of each of the above-identified applications are hereby incorporated by reference.

The invention relates to a universal polypeptidic carrier for targeting molecules to a Gb3 receptor for the B-subunit of Shiga-Toxin expressing cells and its use for intracellular transport and processing of said molecules.

Shiga Toxin is a bacterial toxin of the $AB_5$ subunit family that is secreted by *Shigella dysenteriae*. The A-subunit is the toxic moiety and inhibits the protein synthesis in higher eucaryotic target cells after transfering into the cytoplasm of said cells. The B-subunit is an homopentamer protein (5B—fragments) and is responsible for toxin binding to and internalization into target cells by interacting with the glycolipid Gb3 found on the plasma membranes of these cells. The B-fragment is non toxic, but conserves the intracellular transport characteristics of the holotoxin which, in many Gb3 expressing cells, is transported in a retrograde fashion from the plasma membranes to cytosol, via endosomes.

The glycolipid Gb3 receptor has also been reported to be expressed preferentially in some ectodermic derived tumors (plasma) and some Burkitt's lymphoma. It is also known as CD 77. In the present text, the term Gb3 should be considered as an equivalent to CD77.

The authors have already shown that a CD8 human tumor Antigen fused to the B subunit of Shiga toxin could efficiently be presented in an HLA class I-restricted manner to specific CTL (1). This result was independently confirmed by another study that demonstrated that Shiga holotoxin, carrying a defined peptide epitope from influenza virus, could deliver the antigen into the MHC class I intracellular pathway (3).

The authors have also shown that fusion proteins between the Gb3 receptor-binding non toxic B-fragment of bacterial Shiga toxin derived from *Shigella dysenteriae* and an antigen, or an epitope from a model tumor antigen, can elicit specific cytotoxic T lymphocytes response (CTL), whereas each moiety of said fusion protein does not lead individually to CTL induction (1, 2, and WO 99/03881).

The difficulty of this technology is that, for each application, i.e., for each antigen or fragment thereof, there is a need for a specific construction of a fusion protein, that necessitates a specific construction of a recombinant vector bearing the sequences encoding this fusion protein to be expressed in a host cell.

The aim of the present invention is to overcome the above-mentioned drawbacks and to provide a universal hook, or a universal carrier for targeting a molecule to a Gb3 receptor expressing cell to enable this molecule to be internalized, processed and/or expressed in said cell expressing Gb3 receptor.

In the present invention, a Shiga toxin B-subunit (STxB) derivative, or mutant, termed STxB-Cys has been designed. In this protein, a Cysteine is added at the C-terminus of mature STxB. The protein, when purified from bacteria, carries the internal disulfide bond, as wild type STxB, while the sulfhydryl group at the C-terminal Cys is free. Due to their nucleophilicity, free sulfhydryl groups are excellent acceptors for directed coupling approaches (4).

Thus, the present invention relates to a universal polypeptidic carrier for targeting directly or indirectly a molecule of interest to Gb3 receptor expressing cells having the following formula: STxB-Z(n)-Cys, wherein:
  STxB is the Shiga Toxin B subunit or a functional equivalent thereof,
  Z is an amino-acid devoided of sulfydryl group, n being 0, 1 or an amino-acid sequence,
  Cys being the amino-acid Cysteine.

The STxB moiety of the universal carrier has the sequence described in (8) or a functional equivalent thereof. A functional equivalent means a polypeptidic sequence having the capacity to bind specifically to the Gb3 receptor and/or to trigger an internalization of an antigen and its presentation in an MHC class-I restricted pathway, or both MHC class I and class II on the same antigen presenting cell.

In the light of the heterogeneity of expression of tumor antigens, the allele-specific loss of MHC class I expression at the surface of tumor cells, and the necessity to have concomitant presentation of antigens by both MHC class I and class II on the same antigen presenting cell, it is advantageous to couple full size antigen proteins to the B-subunit for targeting to dendritic cells.

In a preferred embodiment, n is 0 and the universal carrier has the following sequence (SEQ ID No 1):

```
COOH-MKKTLLIAASLSFFSASALATPDCVTGKVE

YTKYNDDDTFTVKVGDKELF

TNRWNLQSLLLSAQITGMTVTIKTNACHNGGGFSEVIFRC-NH2
```

As a matter of fact, if the Z linker is too long, i.e., when n is equal or greater than 2, some internal disulfide bridges might occur, and prevent either the binding of STxB to the Gb3 receptor and especially prevent the binding to the molecule of interest.

According to the invention, the molecule of interest is selected in the group constituted of proteins, peptides, oligopeptides, glycoproteins, glycopeptides, nucleic acids, polynucleotides, or a combination thereof.

In another aspect of the invention, the molecule of interest is an antigen to be targeted to antigen presentating cells. Such cells are selected in a group comprising T lymphocytes, dendritic cells, macrophages Langerhans cells and the like.

In another aspect of the invention, the molecule of interest are drugs such as haptenes, psoralenes, or any compounds provided that they have a chemical group linkable with the —SH group of the Cysteine moiety of STxB-Cys.

The drug might be linked either directly or after activation with coumpounds such as bromoacetate, or any other method known by a skilled person, provided that the result of the reaction is a chemical entity having the following formula: STxB-Cys-M, M being all the above mentioned molecules of interest.

The coupling approaches for covalent binding of a peptidic or a polypeptidic moiety to STxB-Z(n)-Cys can be any method or processes described or carried out by a skilled person.

A first method that can be embodied is the use of SPDP hetero-bi-functional cross-linker described par Carlsson et al (5). However, SPDP is capable of being cleavable by serum thiolases that is a cause of decreasing the yield of the reaction.

A second method for covalent coupling of STxB-Z(n)-Cys peptides with another peptide of interest is to produce bromoacetyl or maleimide functions on the latter as described by P. Schelte et al (4). Briefly, the peptide of interest is chemically activated with bromoacetate anhydride or by a maleimide group respectively. In appropriate reaction conditions (pH, temperature, incubation times), these groups are eliminated by cis-elimination, yielding respectively to —S—S, —S—CH$_2$—, to —S—CO— or to —S—NH— covalents linkages.

As an example, the polypeptide or the peptide to be coupled to the —SH moiety the C-terminal Cysteine of the universal carrier, has its N-terminus activated with bromoacetic anhydride following the reaction scheme:

Br—CH$_2$—CO—O—CO—CH$_2$—Br+
NH$_2$-peptide ⇒ Br—CH$_2$—CO—NH-peptide+
Br—CH$_2$—COOH The Bromoacetyl function has high chemoselectivity for peptide thiol groups and the activated peptide can be reacted with STxB-Cys as follows:

STxB-Cys-SH+Br—CH$_2$—CO—
NH-peptide ⇒ STxB-Cys-S—CH$_2$
—CO—NH-peptide+HBr

The resulting thioether-linkage is stable to hydrolysis.

Another method for coupling a molecule to the universal carrier of the invention is to use MBS (m-Maleimidobenzoyl-N-hydroxysuccinimide ester) as shown in FIG. 6 and explained in example 5. This coupling allows the transport and processing of large molecules such antigenic proteins or glycoproteins through MHC class I and/or MHC class II pathways.

Thus, another aspect of the invention is the product resulting from a covalent binding of STxB-Z(n)-Cys with a molecule of interest by a —S—S—, —S—CO—, or S—CH2- or —S—NH— linkage.

In one embodiment, the molecule of interest to be targeted to an antigen presentating cells is constituted by or comprises a polypeptidic structure, such an antigens or epitopes thereof, glycopeptides or glycoproteins, lipopeptides or lipoproteins.

In a preferred embodiment, the product resulting from the coupling of STxB-Z(n)-Cys with an antigen or a fragment thereof, where (n) is 0, 1, or 2, and preferably 0, is able to be presented in an MHC class I and MHC class II restricted pathway.

In another embodiment, the molecule of interest is a polypeptide capable of binding with polynucleotide structures such as DNA or RNA molecules. Such molecules might be vectors or plasmids comprising a sequence of interest to be expressed in a target cell. In the present invention, a target cell is a eucaryotic cell bearing on its membrane the Gb3 receptor.

Thus, the universal carrier of the present invention is also a carrier for introducing a nucleotide sequence in a target cell either for gene therapy or for obtaining recombinant cells expressing heterologous proteins.

In another embodiment, the universal carrier according to the present invention can be operably linked directly through a covalent binding or indirectly through a linker to a cytotoxic drug to be targeted to tumor cells expressing Gb3 receptor.

The term "indirect binding" means that the universal carrier is covalently linked through the sulfhydryl moiety of the C-terminal Cysteine to a linker, said linker being operably linked to a drug or a pro-drug to be internalized into Gb3 receptor bearing cells.

This linkage might be a covalent binding or a non-covalent binding, provided that the affinity between the linker and the drug (or the pro-drug) is higher than $10^{-9}$ mole/l.

Another aspect of the invention is an isolated polynucleotide selected from the group of.

(a) a polynucleotide comprising the nucleotide sequence STxB encoding the Shiga Toxin B subunit or a functional equivalent thereof bearing at its 3'end the codon TGT, or the codon TGC encoding Cysteine;

b) a polynucleotide comprising a nucleotide sequence having at least 80% sequence identity to a nucleotide sequence encoding the Shiga Toxin B subunit or a functional equivalent thereof bearing at its 3'end the codon TGT or TGC; and c) a nucleotide sequence complementary to the sequence in a) or b).

In a preferred embodiment, the polynucleotide has the following SEQ ID No 2:

5'-atgaaaaaaacattattaatagctgcatcgctttcattttttcag caagtgcgctggcgacgcctgattgtgtaactggaaaggtggagtatac aaaatataatgatgacgatacctttacagttaaagtgggtgataaagaa ttatttaccaacagatggaatcttcagtctcttcttctcagtgcgcaaa ttacggggatgactgtaaccattaaaactaatgcctgtcataatggagg gggattcagcgaagttattttcgttgt-3'

The present invention relates also to a recombinant vector or to a plasmid comprising a polynucleotide sequence as described above, and capable of expressing the universal carrier STxB-Z(n)-Cys, where (n) is 0, 1 or 2, STxB and Z have the same significance as above, in an appropriate host cell.

As an example, a convenient vector is the plasmid pSu108 described in (7).

Another object of the present invention is to provide a method for obtaining a plasmid expressing STxB-Z(n)-Cys comprising:

a) providing a plasmid comprising a STxB sequence;
b) applying two PCR amplification steps using two couples of primers, A' and BB',
A and B being complementary to each other and comprising the Cys codon,
A' and B' being outside the STxB sequence;
c) isolating the amplified fragments;
d) hybridizing the amplified fragments;
e) applying a PCR amplification on the hybridized fragments;
f) insertion of the amplified fragment into a plasmid.

In a preferred embodiment, the plasmid pSU108 (7) containing STxB fragment was modified to introduce the Cysteine codon TGT at the 3' end of the B-fragment cDNA. The primers for step b) are respectively for AA' and BB':

primer A:
(SEQ ID 3)
5'-AGCGAAGTTATTTTTCGTTGTTGACTCAGAATAGCTC-3',
and

```
-continued
primer B:
                                      (SEQ ID n° 4)
5'-GAGCTATTCTGAGTCAACACGAAAAATAACTTC-3', primer A': primer ShigaAtpE:
                                      (SEQ ID n° 5)
5'-CACTACTACGTTTTAAC-3',
and primer B': primer Shiga-fd:
                                      (SEQ ID n° 6)
5'-CGGCGCCTATCGG-3'.
```

The PCR of step e) yields a fragment that is cloned into the SphI and SalI restriction sites of pSU108. Sequences derived by PCR are verified by dideoxy-sequencing.

The skilled person can easily design the choice of primers, plasmids for producing a vector bearing the polynucleotide sequence expressing STxB-Z(n)-Cys in an appropriate host cell, provided that this succession of steps allows the interpretation of the Cys codon into the amplified fragment.

The invention also provides a recombinant cell line obtained by transformation with the recombinant vector containing the polypeptide sequence encoding the universal carrier as described above. In a preferred embodiment, said recombinant cell line is a procaryotic cell, preferentially *E. coli*.

In a still preferred embodiment, the plasmid is pSU108 having SEQ ID No. 2 integrated between the SphI and SalI restriction sites, and the corresponding cell line has been deposited at CNCM on Dec. 19, 2000 with the registration number I-2604.

The present invention also provides a process for producing a universal carrier as described above comprising:
a) culturing a recombinant cell line as described above,
b) obtaining a periplasmic extract of said cells, and
c) purifying said polypeptide.

Preferentially, the cell line is *E. coli* and in c) the purification is made by anion exchange column chromatography followed by a gel filtration column chromatography.

Such a process is particularly advantageous for large scale production of the universal carrier, as far as it can then be operably linked by covalent coupling with a molecule of interest, and used within a large scope of application.

The present invention also provides a method for delivering a sequence of interest into the MHC class I pathway using a product obtained by covalent binding of the Cys moiety of the universal carrier with said sequence of interest; this method is advantageous to elicit a CTL response to a given antigen or epitope thereof as far as the product is specific to the cell involved in the MHC class I pathway.

As a matter of fact, the inventors have shown that an immunodominant peptide, derived from the ovalbumin protein, and coupled chemically to STxB-Cys, could be presented by antigen presenting cells to specific hybridoma cells, demonstrating that STxB could deliver exogenous immunogenic peptide in the MHC class I pathway. To exclude a bias due to the presence of free peptides contaminating the material, experiments using fixed dendritic cells clearly demonstrated that the internalization of the fusion protein was required for this process. The inventors also have shown that the Shiga toxin receptor, $Gb_3$, was also involved in the ability of STxB-Cys to target exogenous peptide in the endogenous MHC class I pathway.

The invention also pertains to a method for delivering an expression vector containing a sequence of interest into a Gb3 receptor expressing cells characterized in that said expression vector is bound to a lysine rich peptide covalently linked to the Cys moiety of the universal carrier.

As an example, the lysine rich peptide is a 16-mer poly-lysine which is able to bind any polynucleotidic sequence, either of DNA or RNA nature. Such a peptide carrying a 16-mer of lysines will be activated at its N-terminus by bromoacetate anhydride and coupled to STxB-Cys. Expression plasmids will be bound to this coupling product, and vectorization of DNA into target cells is assayed using convenient reporter systems, such as the green fluorescent protein or luciferase.

The capacity to target expression plasmids with the help of STxB to the nucleus of antigen presenting cells is expected to further improve the power of this vector, since i) DNA can even more easily be adopted to new experimental or clinical needs, and ii) due to its potentiation effect, expression of antigenic peptides or proteins from DNA would further increase the sensitivity of STxB-dependent antigen presentation.

The invention also provides a method for delivering a drug or a pro-drug into a cell, particularly into a cancer cell bearing Gb3 (or CD77) receptor.

The glycolipid $Gb_3$ receptor has been reported to be preferentially expressed in some neuroectodermic derived tumors (glioma) and some Burkitt's lymphoma. Since one limitation of the use of chemotherapy in cancer is secondary side effects of the drugs because of their toxicity on normal cells, the drugs are preferentially vectorized in tumor cells by using STxB-Cys. The drugs are activated to become reactive with the sulfhydryl group of STxB-Cys. To achieve this, a maleimide group can be introduced on a drug, for example psoralenes compounds.

The present invention also pertains to:
a pharmaceutical composition for enhancing the immunogenicity of a peptide or a protein or a glycoprotein or a lipopeptide, containing the universal carrier covalently linked by its Cys moiety to said peptide or protein or glycoprotein or lipopeptide;
a pharmaceutical composition for treating tumor cells bearing the Gb3 receptor (CD77), containing the universal carrier according to the invention covalently linked by its Cys moiety to a drug or a pro-drug toxic for said tumor cells.

Without limiting the scope of the universal carrier of the invention and its widespread use in different applications, the hereinafter examples and figures illustrate the advantages of the present invention.

LEGEND OF THE FIGURES

FIG. 1 represents the protein profile of the final SephaDex 75 column yielding purified STxB-Cys. Fractions 20-25 contain mostly monomeric STxB-Cys (the positions of monomeric and dimeric STxB-Cys are indicated to the right). Molecular weight markers are indicated to the left.

FIG. 2a represents the coupling of Type2 of Pep2 [as defined in example 2] to STxB-Cys, followed by an in vitro antigen presentation assay on D1 dendritic cells, as described in (2). Two different preparations of STxB-Cys coupled to the SL8 peptide, an immunodominant epitope of ovalbumin were used (termed 4A and 9A). Upon fixation, antigen presentation is abolished showing that no extracellular processing occurred.

Figure 6:
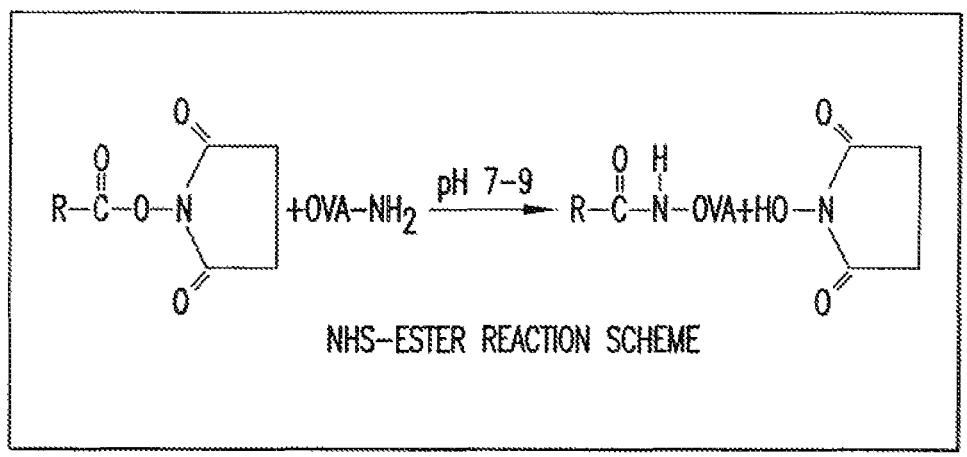
Figure 6:
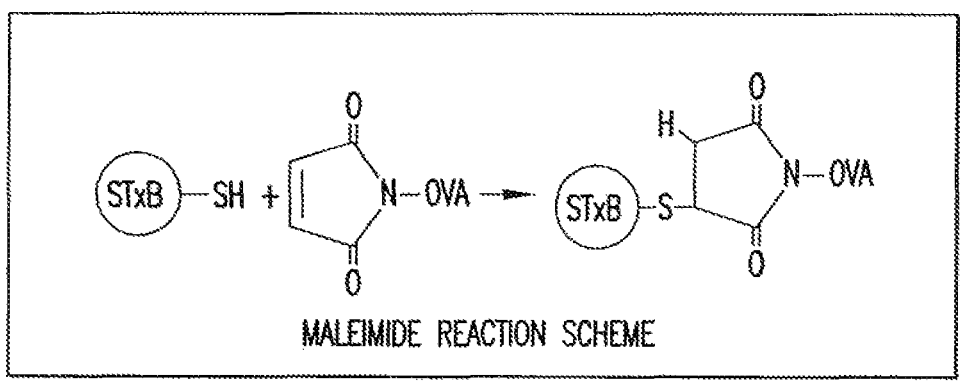
Figure 6:
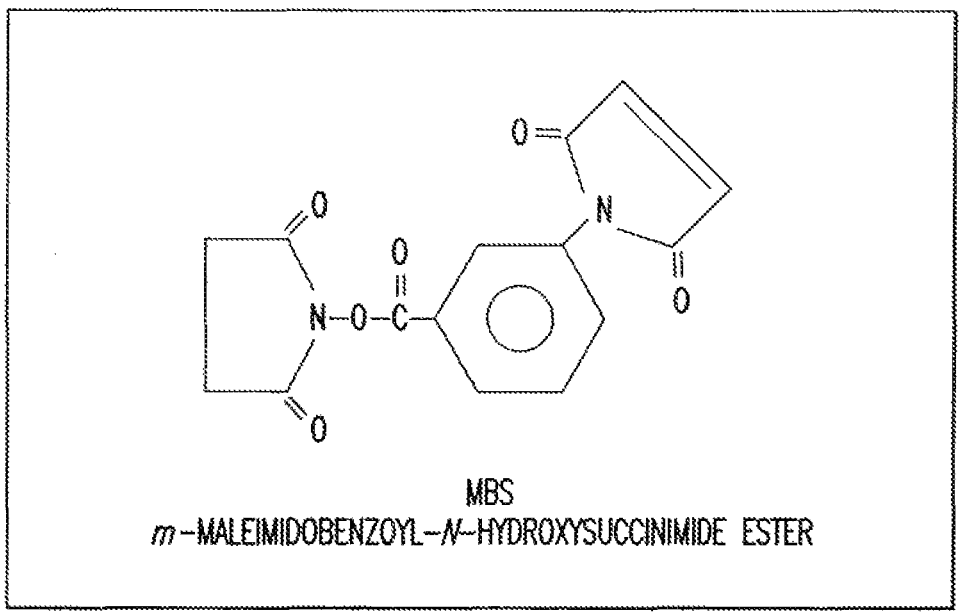

FIG. 6 represents reaction scheme for full size Ova coupling to STxB-Cys using the heterobifunctional cross linker MBS. Top: first reaction linking MBS to primary amines of Ova. Middle: second reaction between activated Ova and STxB-Cys. Bottom: Structure of MBS.

Figure 7:
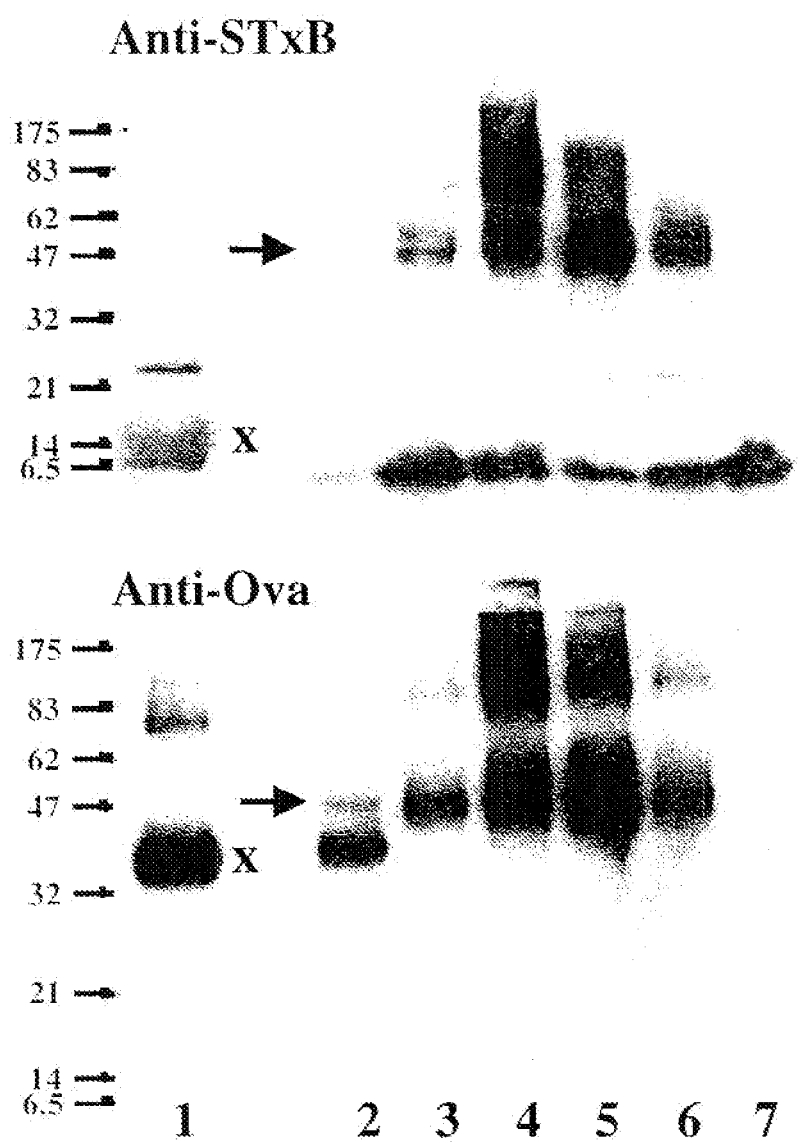

FIG. 7 shows western analysis of Ova coupling to STxB-Cys. The upper part of the figure represents an immunoblot using anti-STxB antibody, the lower part an immunoblot using anti-Ova antibody. The intermediates of different steps of the purification procedure are shown. Lane 1: uncoupled proteins (marked by a cross). Lane 2: coupling reaction (coupling product marked by an arrow). Lane 3: eluate of the immunoaffinity column doted with anti-STxB antibody. Lanes 4-7: fractions from the gelfiltration column. Lane 4: fractions 9-10. Lane 5: fractions 11-12. Lane 6: fractions 13-14. Lane 7: fractions 15-19 (free STxB-Cys). Fractions 11-12 contain the bulk of monomeric coupling product. Some material with lower electrophoretic mobility can also be detected, originating likely from dimeric Ova present in the original preparation.

Figure 8:
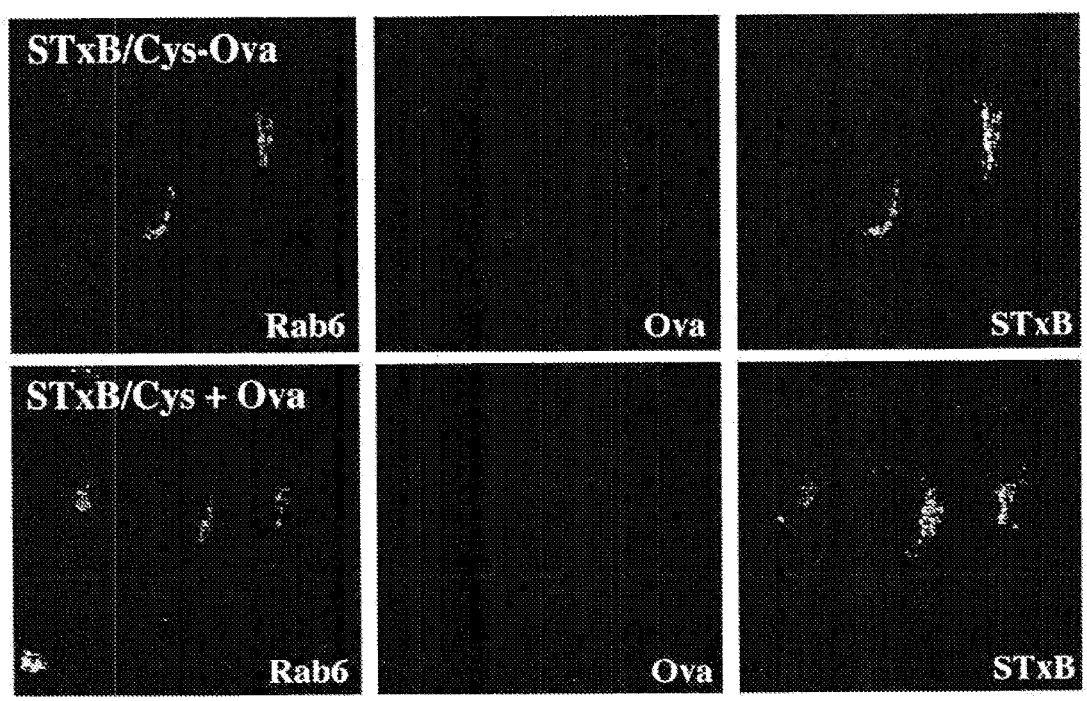

FIG. 8 represents immunofluorescence analysis of STxB-Cys-Ova transport in HeLa cells. The coupling product STxB-Cys-Ova (upper part of the figure) or a mixture of STxB-Cys and Ova (lower part of the figure) were incubated with HeLa cells on ice. After washing, the cells were shifted for 45 min to 37° C., fixed, and stained with the indicated antibodies. Note that when Ova is linked to STxB-Cys (top), the protein is vectorized into the Golgi apparatus, co-stained for the Golgi marker Rab6. If Ova is only mixed with STxB-Cys (bottom), the protein cannot be detected on the cells.

Figure 9B:
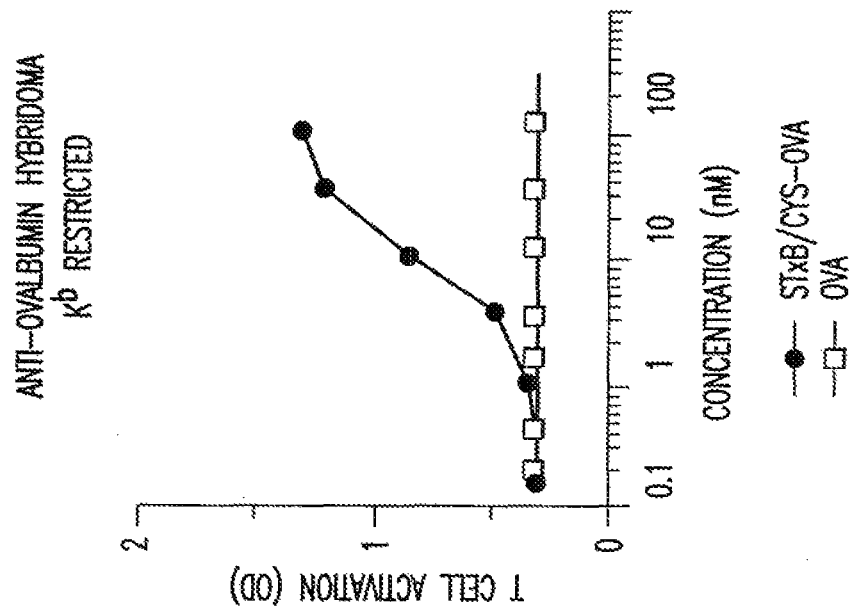
Figure 9A:
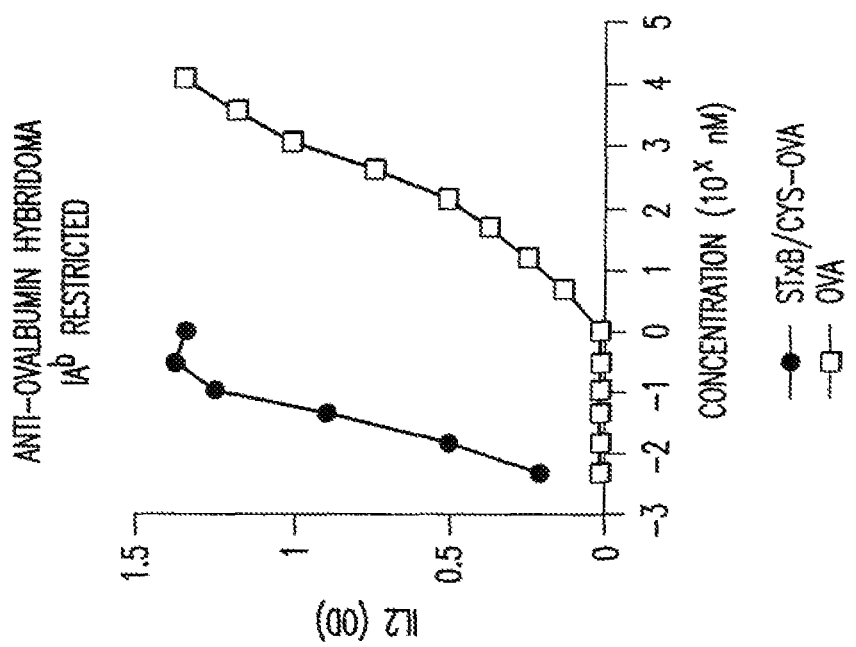

FIG. 9a shows MHC class I and II restricted antigen presentation using STxB-Cys-Ova$_{329-339}$ used to sensitize the murine dendritic cell line D1.

FIG. 9b shows MHC class I and II restricted antigen presentation using STxB-Cys-Ova$_{257-264}$ and the immunodominant SL8 Ova-derived peptide alone used to sensitize the murine dendritic cell line D1.

EXAMPLE 1

Figure 1:
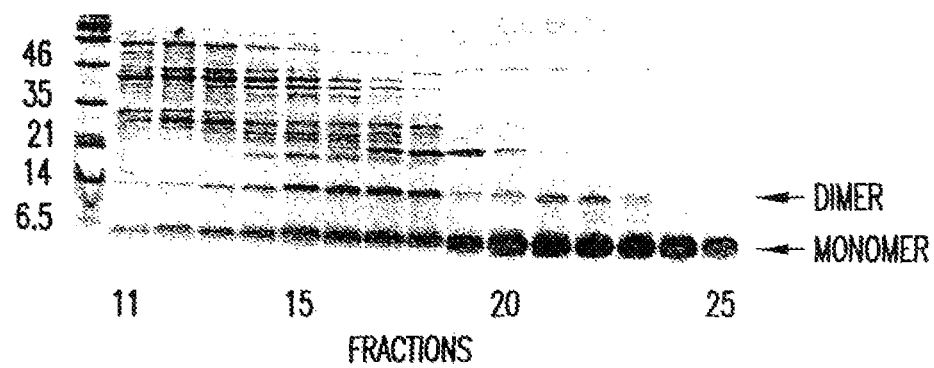

Preparation of the Universal Carrier a) Construction of a Plasmid Expressing STxB-Cys:

In a preferred embodiment, the plasmid pSU108 (7) was modified to introduce the Cysteine codon tgt at the 3' end of the B-fragment cDNA. PCR primer A: SEQ ID no 3 (5'-AGCGAAGTTATTTTTCGTTGTTGACTCA-GAATAGCTC-3') and primer A': SEQ ID no 4 (5'-GAGC-TATTCTGAGTCAACACGAAAAATAACTTC-3') were used with plasmid specific primers ShigaAtpE: SEQ ID no 5 (5'-CACTACTACGTTTTAAC-3') and Shiga-fd: SEQ ID no 6 (5'-CGGCGCAACTATCGG-3') to produce DNA fragments which, in a second PCR with primers Shiga AtpE and Shiga-fd yielded a fragment that was cloned into the SphI and SalI restriction sites of pSU108. Sequences derived by PCR were verified by dideoxy-sequencing.

b) Protein Purification:

b) 1. Preparation of the Periplasmic Extract was Performed as Follows:

Inoculate 125 ml of LB/Amp with 125 µl of an overnight culture grown at 30° C., grow over night at 30° C., transfer into 375 ml of LB/Amp at 50° C.; incubate 4 hours at 42° C., centrifuge to pellet cells, wash cells 3 times with 10 mM Tris/HCl, pH 8.0, re-suspend cells in 200 ml of 25% sucrose, 1 mM EDTA, 10 mM Tris/HC1, Ph 8.0; incubate at room temperature for 10 min., centrifuge to pellet cells, re-suspend cells in 200 ml of ice cold water containing a protease inhibitor cocktail; incubate on ice for 10 min., centrifuge; collect supernatant; add 20 mM Tris/HC1, Ph8.0.

b) 2. Purification on Columns:

The periplasmic extract was loaded on a QFF anion exchanger column (pharmacia) and eluted at 230 mM NacI. STxB-Cys containing fractions are pooled, diluted 4-fold and loaded on a Mono Q anion exchanger column (pharmacia), followed by elution at 230 mM NacI. After concentration with microconcentration devices from PallFiltron, the pooled fractions were passed through a Sephadex 75 gel filtration column. Purity was above 95% (FIG. 1).

b) 3. Product Characterization:

The B-fragments of STxB-Cys, purified from Sephadex 75 gel filtration columns, are essentially monomeric (FIG. 1). This is in marked difference to constructions where the Cysteine was added at more than 2 amino acids from the natural C-terminus of the B-fragment. In these cases, neighbouring B-fragments within a pentamer are engaged in disulfide bonds.

EXAMPLE 2

Conditions for Coupling of Activated Peptides to the Universal Carrier a) Carriers:

Three different carriers have been compared.

1) STxB-Cys: B-fragment to which a Cys has been added right to its C-terminus. This protein elutes as a monomer from the purification columns.

2) STxB-Z$_2$-Cys: carrier with a short spacer (2 amino acids resulting from a cloning cassette) between the C-terminus of the wild type B-fragment and the Cys. The majority of the protein eluted as dimers from the purification columns. These can be separated under reducing conditions, indicating the formation of disulfide bonds between monomers in the pentameric B-subunit complex.

3) STxB-Glyc-Cys-KDEL: carrier in which the Cys is located between a Glycosylation cassette being 9 amino acid long and a C-terminal KDEL peptide. The majority of the protein eluted as dimers from the purification columns. These can be separated under reducing conditions, indicating the formation of disulfide bonds between monomers in the pentameric B-subunit complex.

b) Test Peptides:

1) Pep1: a synthetic peptide of 16 amino acids carrying the SL8 antigenic peptide derived from chicken ovalbumin.

2) Pep2: a synthetic peptide of 24 amino acids as above with, in addition, a His-gag at its C-terminus.

3) SL8: the antigenic peptide from ovalbumin that can directly exchange with peptides on MHC class I complexes at the plasma membrane of antigen presenting cells.

c) Coupling Conditions:

Under reducing conditions (Type1): Fusion proteins were treated with DTT overnight, then activated peptide (carrying a bromo acetate group at its N-terminus) was added in excess. Conditions used for the first coupling experiments using fusion proteins will mostly dimerize monomers (proteins STxB-$Z_2$-Cys and STxB-Glyc-Cys-KDEL).

Under non-reducing conditions (Type2): Fusion proteins are directly reacted with the activated peptides.

d) Biochemical and Morphological Controls:

Pep2 carries a His-tag. This has allowed us, using an anti-His antibody, to show the presence of Pep2 on B-subunit by Western blotting, and the B-subunit dependent transport of Pep2 in HeLa cells.

Figure 2A:
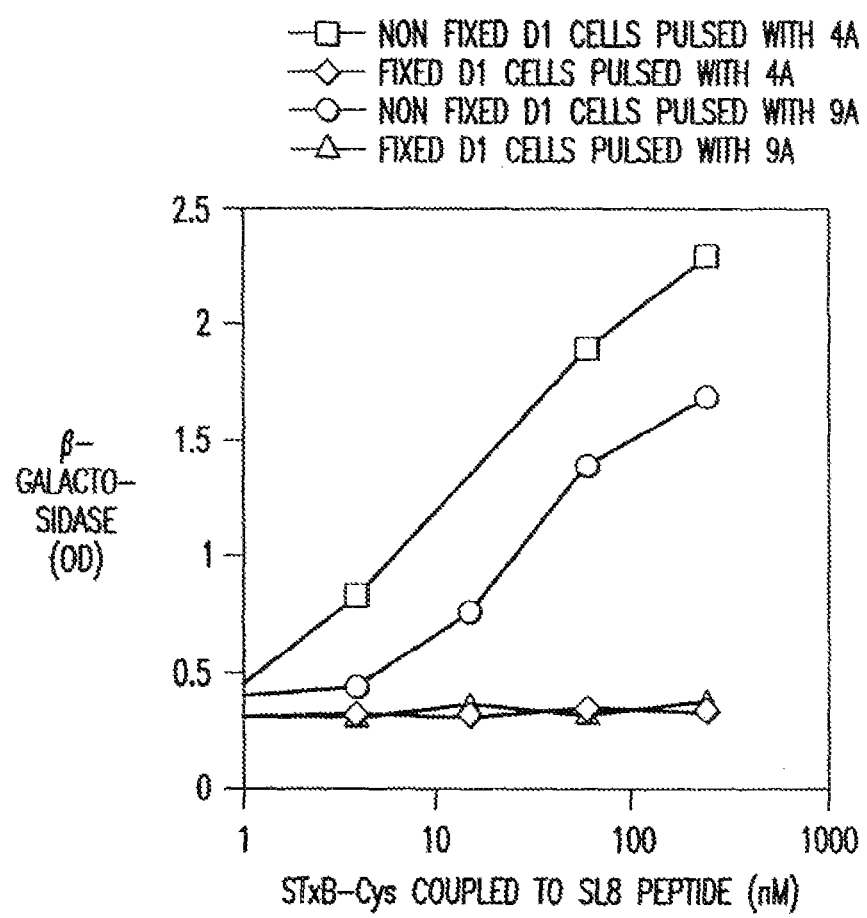
FIG. 2b represents a control experiment of FIG. 2a, in which it is shown that fixed D1 can still present free SL8 peptide.

FIG. 2a shows that a dose dependent stimulation of the B3Z CTL hybridoma (measurement of β-galactosidase activity) was observed with non-fixed cells, while fixation abolished antigen presentation.

Note that antigen presentation only works on non-fixed cells, indicating that the observed presentation does not result from contaminating free Pep2.

Figure 2B:
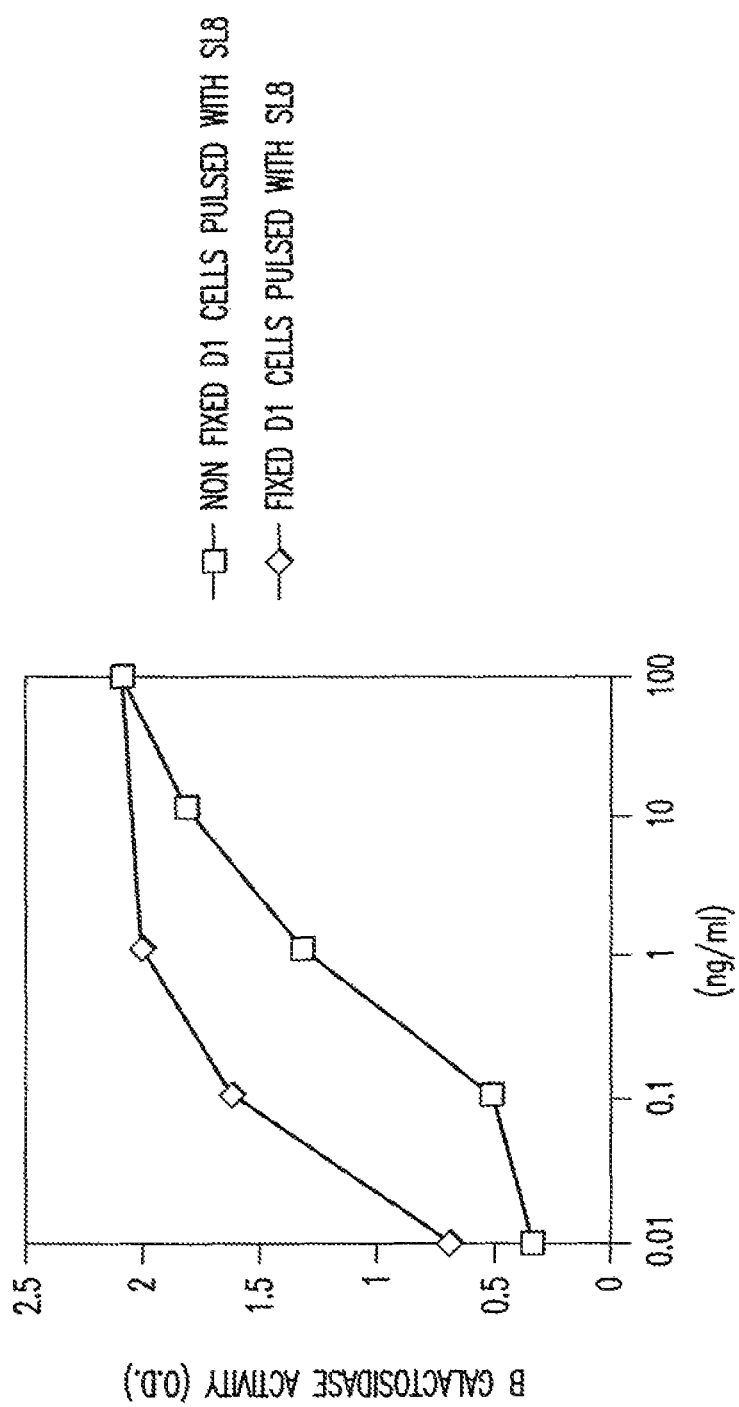

FIG. 2b shows the control experiment of FIG. 2a in which it is shown that fixed D1 cells can still present free SL8 peptide.

Figure 3:
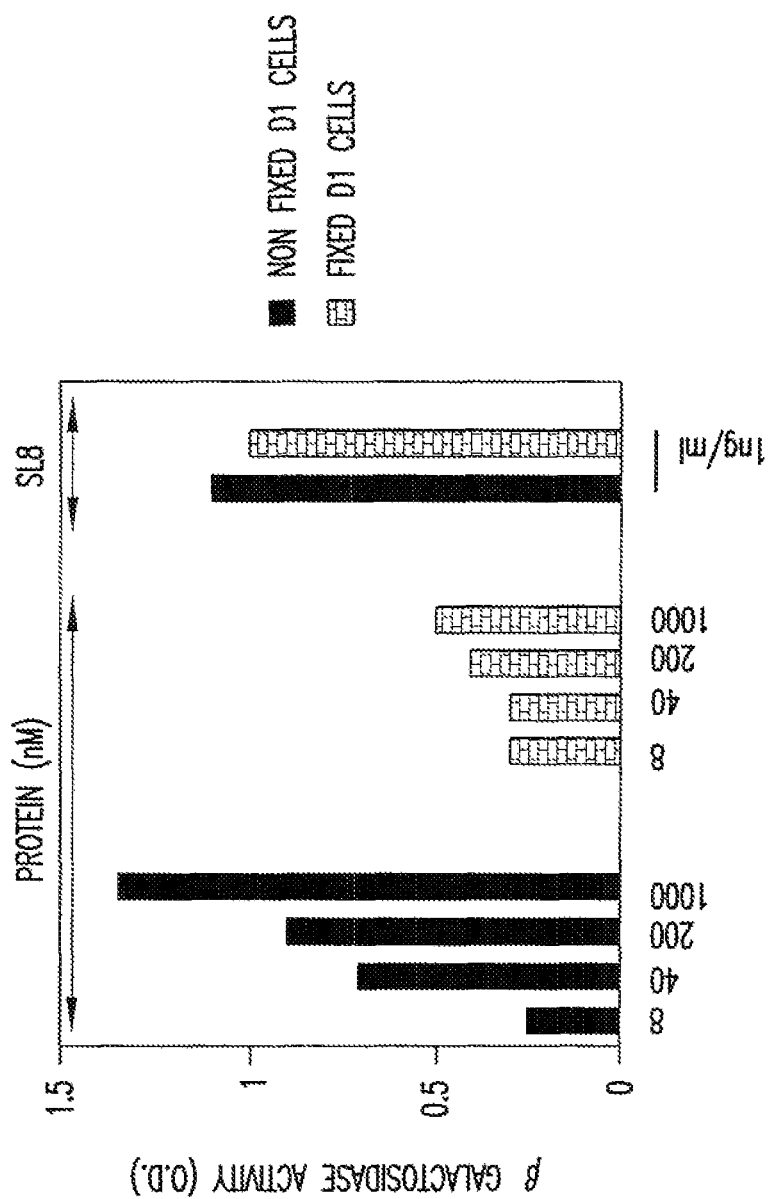
FIG. 3 represents another experiment on fixed and non fixed D1 cells using a coupling reaction of Type1 on STxB-SH and Pep1 [as defined in example 2].

In FIG. 3, it appears that in this type of protocol, some free Pep1 appears to co-purify with the fusion protein, since at high doses (200-1000 nM), some presentation was observed on fixed cells. Presentation by SL8 is shown to the right.

Figure 4:
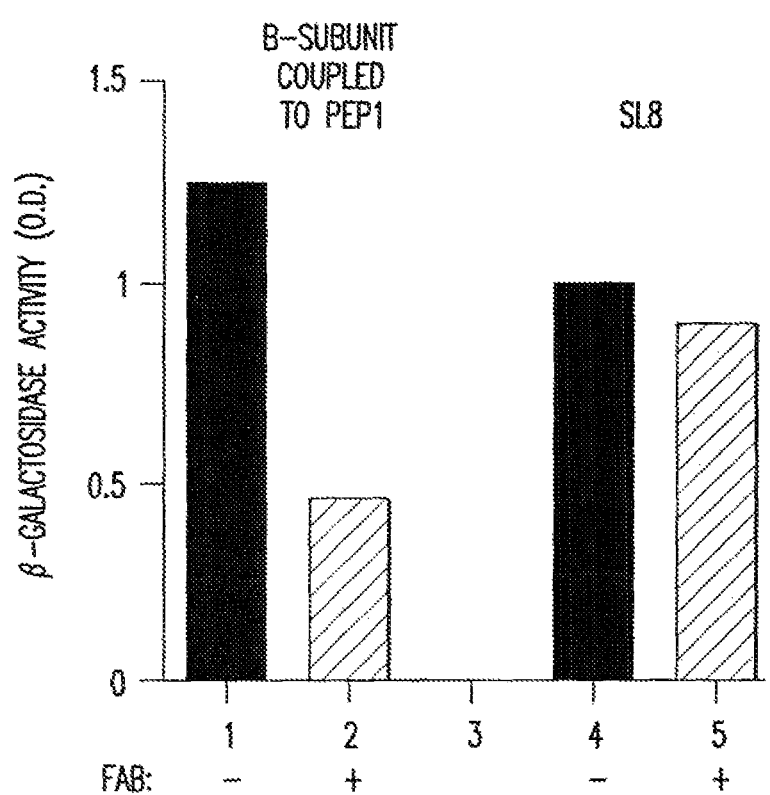
FIG. 4 represents the B-subunit dependent presentation of antigenic peptides derived from a coupling of Pep2 to B-Glyc-Cys-KDEL. The use of Fab fragments from an antibody that neutralize STxB binding to Gb3 also abolishes antigen presentation.

In FIG. 4, the coupled protein (lanes 1 and 2) or the SL8 Peptide (lanes 5 and 6) were incubated (lanes 2 and 5) or not (lanes 1 and 4) with anti-B-subunit Fab-fragment derived from the 13C4 antibody which inhibits the binding of the B-subunit to Gb3. Note that the Fab-fragment neutralizes the capacity of the B-subunit to introduce the antigenic peptide into the class I pathway, while the presentation with SL8 is not affected under these conditions. The background signal in this experiment was at 0.3.

Figure 5A:
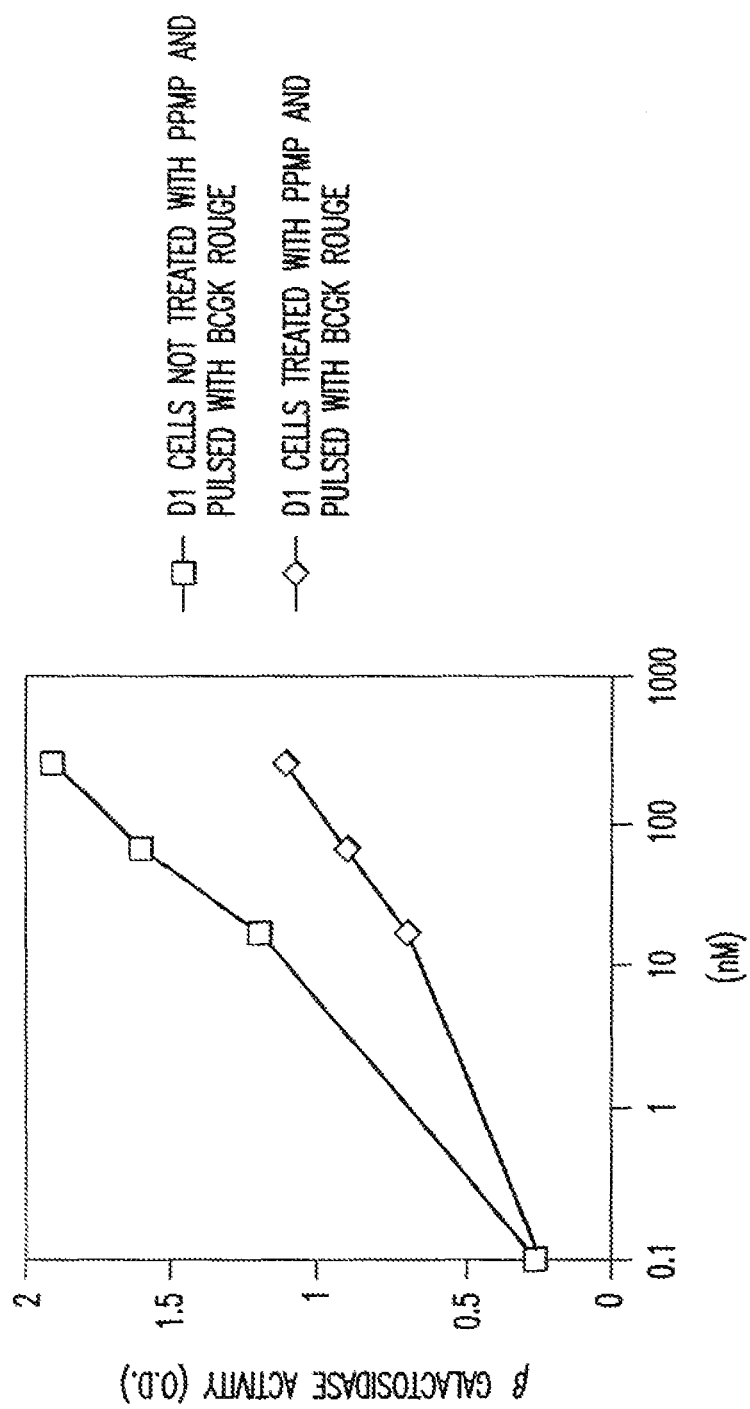
FIG. 5a shows that the Gb3 synthesis inhibitor PPMP inhibits B-subunit dependent antigen presentation and FIG. 5b shows that SL8 presentation is not decreased in PPMP treated cells.
Figure 5B:
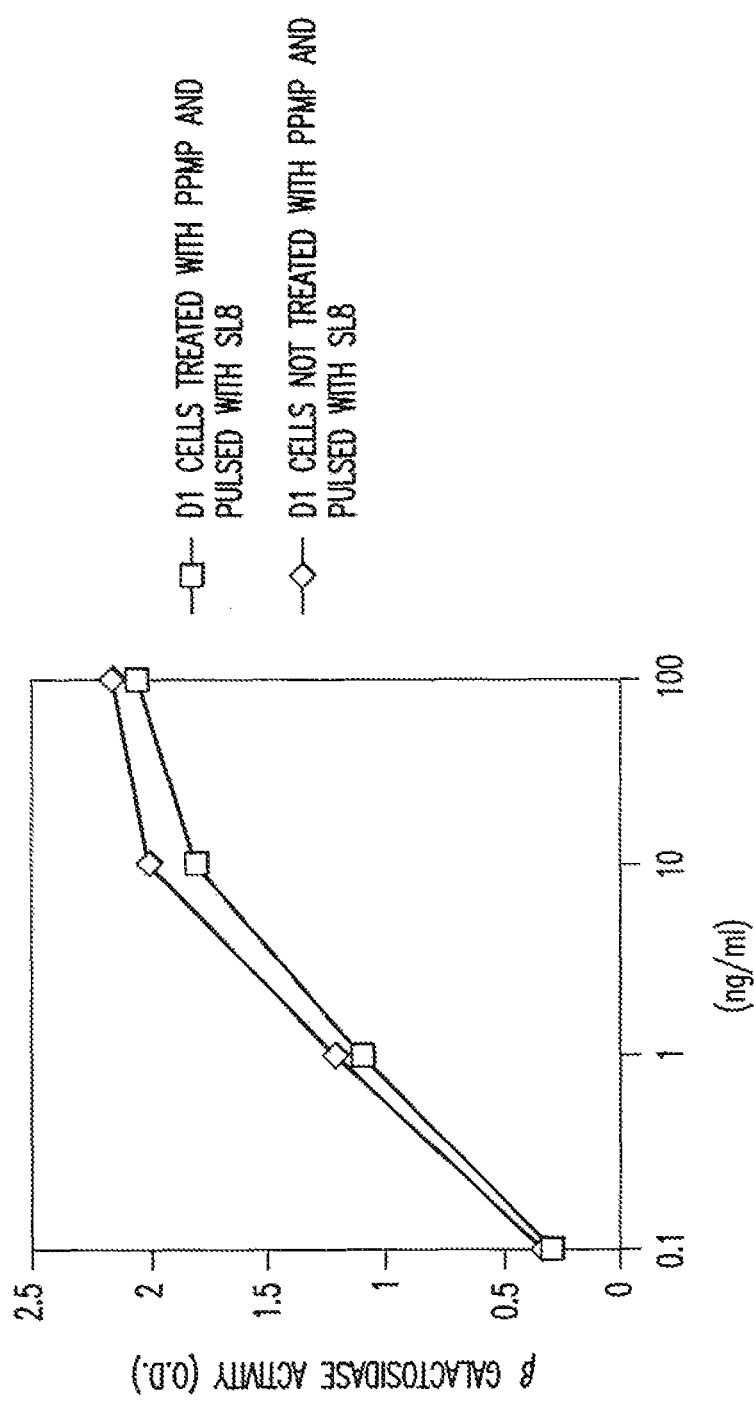

In FIG. 5a, $D_1$ cells were pre-treated with PPMP (see FIG. 3b of (2)) for 3 days. This treatment lead to an important decrease of Gb3 expression at the cell surface, without however eliminating it completely. Under this condition, antigen presentation from a coupling reaction of Pep1 with STxB-Glyc-Cys-KDEL was significantly reduced, indicating that Gb3 is important for the presentation phenomena.

It appears from all these experiments that the coupling under non-reducing to STxB-Cys is surprisingly efficient (in terms of sensitivity; note that, as shown in FIG. 1, only 4 nM of STxB-Cys-Pep2 are necessary to have a response). Thus, the universal carrier STxB-Cys is preferred due to its simplicity in its preparation and to the reproducibility of the coupling.

Hence, the optimal conditions for coupling of activated peptides to STxB-Cys were the following:
dialyse STxB-Cys against 20 mM Borate buffer, pH 9.0, 150 mM NaCl,
concentrate to 1 mg/ml,
dissolve N-terminally activated peptide (activated with bromoacetate anhydride) at 12 mM in DMSO,
dilute peptide to 0.2 mM in protein solution,
incubate 12 hours at room temperature,
dialyse against PBS.

EXAMPLE 3

Characterization of TxB as to its Antigen Presentation Capacity

The following experimental series will help to fully describe the capacity of STxB to function in antigen presentation system.

a) Class I- and Class II-restricted Antigen Presentation:

A peptide carrying class I- and II-restricted antigenic peptides from chicken ovalbumin (Br—CH2-CO—NH-LEQLESIINFEKLTEWSLKISQAVHAAHAEINEAGR (SEQ ID NO:6), sequences 257-264 and 323-339 were coupled to STxB-Cys, and the class I- and class II-restricted presentation of these peptides were assayed using the corresponding T-cell hybridomas.

b) Coupling of Whole Size Proteins.

Our preliminary evidence suggests that chicken ovalbumin can be coupled to STxB-Cys. These experiments have been done with the SPDP heterobifunctional cross-linker. (Carlsson et al., 1978).

A first series of antigen presentation experiments indicated that the ovalbumin protein can be introduced into the endogenous MHC class I-restricted antigen presentation pathway of mouse dendritic cells. SPDP has the inconvenience of being cleavable by serum thiolases. This cross-linker was successfully substituted by MBS which is non-cleavable. Other antigenic proteins (Mart 1 and polypeptides derived from HPV16-E7 and Muc1) are tested to show that the procedure is of universal use.

c) Coupling of Complex Protein Mixtures.

A lysate from the cervix carcinoma-derived cell line Caski is used. This cervix carcinoma cell line, which expresses the HLA-A2 allele at its membrane, also expresses Human papillomavirus derived peptides. E7 is a early transcribed ORF from HPV which is necessary for transformation of primary keratinocytes. Since anti-E7 HLA A2-restricted CTL are elicited in vitro. The efficacy of the coupling of this protein mixture by a presentation assay specific for HLA-A2 E7 derived peptides was tested. As control, a lysate from a HLA-A2-positive cell line which does not express E7 (croft cells or Daudi) was coupled to STxB-lys.

EXAMPLE 4

Application to MHC Class I-restricted Antigen Presentation

The experiment of FIG. 4 shows that STxB-Cys dependent antigen presentation is inhibited when the interaction with $Gb_3$ is abolished. Here it is found that pre-binding of the Fab fragment of monoclonal Ab against STxB to 0.1 μM STxB-Cys, coupled to SL8, inhibited antigen presentation, suggesting that STxB-Cys binding to $Gb_3$ is necessary for antigen presentation. Similar results were obtained when $Gb_3$-expression was inhibited with a drug (FIG. 4).

EXAMPLE 5

Reaction Chain for Coupling Ovalbumine to the STxB-Cys

The reaction scheme is shown in FIG. 6.

In a first reaction, the N-hydroxysuccinimide ester moiety of MBS reacts with primary amines on an antigenic target protein, such as the model protein ovalbumin (Ova). The reaction product is purified and then incubated in a second reaction with STxB-Cys leading to coupling via the maleimidobenzoyl moiety.

FIG. 7 shows the SDS-PAGE and Western analysis of a typical coupling reaction involving STxB-Cys and Ova. For coupling, 20 mg/ml of Ova in 100 mM HEPES, pH 7.4, was incubated with 4.5 mM of MBS for 30 min at room temperature. The reaction is passed through a PBS/EDTA 10 mM equilibrated gel filtration column. Eluted Ova is concentrated to 20 mg/ml. 1 volume of STxB-Cys at 3.5 mg/ml in PBS/EDTA is mixed with 1 volume of activated Ova and incubated over night at room temperature.

FIG. 7 shows that within the coupling reaction, bands with lower electrophoretic mobility (labeled with arrows; coupling product) can be detected in addition to uncoupled STxB (upper part) and uncoupled Ova (lower part; uncoupled proteins are labeled with a cross). The reaction product is purified by passage through an immunoaffinity column made with 13C4 anti-STxB monoclonal antibody (lane IP column). Note that free Ova is eliminated. Eluted STxB-Cys (coupled and non-coupled) is then passed through a gel filtration column to separate free STxB (fractions 15-19) from coupled STxB-Cys (fractions 9-14; note that fractions 11-12 contain the bulk of coupled protein; the upper coupling band, which is minor compared to the lower band, probably results from dimeric Ova).

EXAMPLE 6

Intracellular Transport Characteristics of STxB-Cys-Ova Coupling Product 0.5 µM of STxB-Cys-Ova was incubated with HeLa cells on ice. The cells were washed and shifted to 37° C. for 45 min, fixed, and stained for the indicated antibodies. As shown in FIG. 8, when STxB-Cys and Ova were linked by MBS, Ova immunoreactivity could be detected together with STxB immunoreactivity in the Golgi apparatus, stained by Rab6. When both proteins are incubated as separate entities with HeLa cells, only STxB-Cys is transported to the Golgi, while Ova cannot be detected on the cells. These data clearly show that couples STxB-Cys is still transported in the same manner as uncoupled STxB-Cys, and that Ova is vectorized via STxB-Cys.

EXAMPLE 7

The STxB-Cys Allows Both, MHC Class I and II Restricted Presentation of Peptides Derived from Full Size Exogenous Antigenic Proteins In a first experiment (FIG. 9, left), we have shown that when STxB-Cys-Ova is used to sensitize the murine dendritic cell line D1, a clear increase of the presentation of the MHC class II restricted Ova derived peptide $Ova_{323-339}$ is observed, compared to D1 cells pulsed with non-vectorized Ova. Indeed, a significant presentation of $Ova_{323-339}$ peptide could be detected with as little as 0.01 nM of STxB-Cys-Ova, whereas 10 nM of full size Ova was required for an efficient presentation of the same peptide. The presentation of the $IA^b$ restricted $Ova_{323-339}$ peptide was revealed using the B097.10 hybridoma that produces IL-2 after recognition of this peptide. As a control, we did not observe IL-2 secretion when an irrelevant MHC class II restricted hybridoma was used instead of B097.10 (data not shown).

In a second experiment, we have pulsed the same D1 dendritic $H2^b$ restricted cell line with either Ova alone or with STxB-Cys-Ova. No presentation of the Ova-derived immunodominant SL8 peptide ($Ova_{257-264}$) was observed when the D1 cells were sensitized with up to 100 nM of free Ova, while 1-10 nM of STxB-Cys-Ova allowed the presentation of the SL8 peptide, as revealed by the specific B3Z hybridoma that recognize the SL8 peptide in the context of $K^b$ molecules. As a control, it was shown that no activation of an irrelevant hybridoma was observed under the same experimental conditions.

Altogether, these results clearly demonstrate that STxB-Cys targets full size proteins with high efficiency into both, the MHC class I and class II pathways.

BIBLIOGRAPHY (1) Ren-Shiang Lee, Eric Tartour, Pierre van der Bruggen, Valérie Vantomme, Isabelle Joyeux, Bruno Goud, Wolf Herman Fridman and Ludger Johannes, "Major histocompatibility complex class I Presentation of exogenous soluble tumor antigen fused to the B-fragment of Shiga toxin". Eur. J. Immunol. (1998) 28: 2726-2737.

(2) Nacilla Haicheur, Emmanuelle Bismuth, Sophie Bosset, Olivier Adotevi, Guy Warnier, Valérie Lacabanne, Armelle Regnault, Catherine Desaymard, Sebastian Amigorena, Paola Ricciardi-Castagnoli, Bruno Goud, Wolf H. Fridman, Ludger Johannes and Eric Tartour, "The B Subunit of Shiga Toxin Fused to a Tumor Antigen Elicits CTL and Targets Dendritic Cells to Allow MHC Class I-Restricted Presentation of Peptides Derived from Exogenous Antigens". The Journal of Immunology (2000) 10: 3301-3308.

(3) Noakes, K. L., H. T. Teisseranc, J. M. Lord, P. R. Dunbar, V. Cerundolo and L. M. Roberts "Exploiting retrograde transport of Shiga-like toxin 1 for the delivery of exogenous antigens into the MHC class I presentation pathway". Febs. Lett. (1999) 453:95.

(4) Philippe Schelté, Christophe Boeckler, Benoît Frisch and Francis Schuber "Differential Reactivity of Maleimide and Bromoacetyl functions with Thiols: Application to the Preparation of Liposomal Diepitope Constructs". Eur. J. Immunol. (1999) 29:2297-2308.

(5) Carisson, J., H. Drevin, and R. Axen. 1978. Protein thiolation and reversible protein-protein conjugation. N-Succinimidyl 3-(2-pyridyldithio)propionate, a new heterobifunctional reagent. *Biochem. J.* 173:723-737.

(6) Su, G. F., H. N. Brahmbhatt, J. Wehland, M. Rohde and K. N. Timmis "Construction of stable LamB-Shiga toxin B subunit hybrids: analysis of expression in *Salmonella typhimurium* aroA strains and stimulation of B subunit-specific mucosal and serum antibody responses". (1992) Infect. Immun. 60:3345-3359.

(7) Johannes, L., Tenza, D., Antony, C. and Goud, B., "Retrograde transport of KDEL-bearing B-fragment of Shiga toxin". (1997) J. Biol. Chem. 272: 19554-19561.

(8) N. A. Stockbine, M. P. Jackson, L. M. Sung, R. K. Holmes, A. D. O'Brien, J Bacteriol 170, 1116-22 (1988).

The invention claimed is:

1. An isolated polynucleotide selected from the group consisting of:
   a) a polynucleotide comprising the nucleotide sequence STxB encoding the Shiga Toxin B subunit or a functional equivalent thereof bearing at its 3' end the codon TGT, or the codon TGC encoding cysteine, wherein the functional equivalent thereof binds to the Gb3 receptor and triggers the internalization of an antigen and its presentation in an MHC class I and MHC class II restricted pathway on the same antigen presenting cell;
   b) a polynucleotide comprising a nucleotide sequence having at least 80% sequence identity to a nucleotide sequence encoding the Shiga Toxin B subunit or a functional equivalent thereof, bearing at its 3' end the codon TGT or TGC, wherein the functional equivalent thereof binds to the Gb3 receptor and triggers the internalization of an antigen and its presentation in an MHC class I and MHC class II restricted pathway on the same antigen presenting cell and
   c) a nucleotide sequence complementary to the sequence in a) or b).

2. The polynucleotide according to claim 1, comprising SEQ ID No. 2.

3. A recombinant vector or plasmid, comprising a polynucleotide sequence according to claim 1.

4. A recombinant cell line obtained by transformation with the recombinant vector according to claim 3.

5. The recombinant cell line according to claim 4, which is a prokaryotic cell line.

6. The recombinant cell line according to claim 5, which prokaryotic cell line is *E. coli*.

7. The recombinant cell line according to claim 6, deposited at the CNCM on Dec. 19, 2000 under accession number I-2604.

8. A method for constructing a recombinant vector according to claim 3 comprising:
   a) providing a plasmid comprising a STxB sequence;
   b) applying two PCR amplification steps using two couples of primers AA' and BB' wherein A and B are complementary to each other and comprise the Cys codon and A' and B' are outside the STxB sequence;
   c) isolating the amplified fragments;
   d) hybridizing the amplified fragments;
   e) applying a PCR amplification on the hybridized fragments; and
   f) inserting the amplified fragments into a plasmid.

9. The method according to claim 8, wherein in step f) the fragments are inserted into a SphI and SalI restriction site of the plasmid pSU108.

10. A process for producing an isolated polypeptide comprising:
    a). culturing a recombinant cell line of claim 4;
    b) obtaining a periplasmic extract of said cells; and
    c) purifying said polypeptide.

11. The process according to claim 10 wherein in step a) the cell line is *E. coli* and in step c) the purification is by anion exchange column chromatography followed by a gel filtration column chromatography.

* * * * *

SEQUENCE LISTING

<160> NUMBER OF SEQ ID NOS: 7

<210> SEQ ID NO 1
<211> LENGTH: 90
<212> TYPE: PRT

<213> ORGANISM: Artificial Sequence
<220> FEATURE:
<223> OTHER INFORMATION: Synthetic peptide: Universal Carrier

<400> SEQUENCE: 1

```
Met Lys Lys Thr Leu Leu Ile Ala Ala Ser Leu Ser Phe Phe Ser Ala
 1               5                  10                  15

Ser Ala Leu Ala Thr Pro Asp Cys Val Thr Gly Lys Val Glu Tyr Thr
                20                  25                  30

Lys Tyr Asn Asp Asp Asp Thr Phe Thr Val Lys Val Gly Asp Lys Glu
            35                  40                  45

Leu Phe Thr Asn Arg Trp Asn Leu Gln Ser Leu Leu Leu Ser Ala Gln
    50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg Cys
                85                  90
```

<210> SEQ ID NO 2
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 2

```
atgaaaaaaa cattattaat agctgcatcg ctttcatttt tttcagcaag tgcgctggcg      60
acgcctgatt gtgtaactgg aaaggtggag tatacaaaat ataatgatga cgatacccttt    120 acagttaaag tgggtgataa agaattattt ccaacagat ggaatcttca gtctcttctt     180
ctcagtgcgc aaattacggg gatgactgta accattaaaa ctaatgcctg tcataatgga    240
gggggattca gcgaagttat ttttcgttgt                                      270
```

<210> SEQ ID NO 3
<211> LENGTH: 37
<212> TYPE: DNA
<213> ORGANISM: Artificial Sequence
<220> FEATURE:
<223> OTHER INFORMATION: Synthetic Primer A

<400> SEQUENCE: 3

```
agcgaagtta ttttcgttg ttgactcaga atagctc                              37
```

<210> SEQ ID NO 4
<211> LENGTH: 33
<212> TYPE: DNA
<213> ORGANISM: Artificial Sequence
<220> FEATURE:
<223> OTHER INFORMATION: Synthetic Primer B

<400> SEQUENCE: 4

```
gagctattct gagtcaacac gaaaaataac ttc                                 33
```

<210> SEQ ID NO 5
<211> LENGTH: 17
<212> TYPE: DNA
<213> ORGANISM: Artificial Sequence
<220> FEATURE:
<223> OTHER INFORMATION: Synthetic Primer A'
<220> FEATURE:
<221> NAME/KEY: misc_feature
<222> LOCATION: (1)..(17)
<223> OTHER INFORMATION: Primer ShigaAtpE -continued

```
<400> SEQUENCE: 5
cactactacg ttttaac                                                  17

<210> SEQ ID NO 6
<211> LENGTH: 15
<212> TYPE: DNA
<213> ORGANISM: Artificial Sequence
<220> FEATURE:
<223> OTHER INFORMATION: Synthetic Primer B'
<220> FEATURE:
<221> NAME/KEY: misc_feature
<222> LOCATION: (1)..(15)
<223> OTHER INFORMATION: Primer Shiga-fd

<400> SEQUENCE: 6
cggcgcaact atcgg                                                    15

<210> SEQ ID NO 7
<211> LENGTH: 36
<212> TYPE: PRT
<213> ORGANISM: Artificial Sequence
<220> FEATURE:
<223> OTHER INFORMATION: synthetic peptide derived from chicken
      ovalbumin

<400> SEQUENCE: 7

Leu Glu Gln Leu Glu Ser Ile Ile Asn Phe Glu Lys Leu Thr Glu Trp
 1               5                  10                  15

Ser Leu Lys Ile Ser Gln Ala Val His Ala Ala His Ala Glu Ile Asn
                20                  25                  30

Glu Ala Gly Arg
            35
```